United States Patent [19]
Racchini

[11] Patent Number: 5,569,198
[45] Date of Patent: Oct. 29, 1996

[54] MICROPOROUS CATHETER

[75] Inventor: Joel R. Racchini, Edina, Minn.

[73] Assignee: CorTrak Medical Inc., Minneapolis, Minn.

[21] Appl. No.: 376,765

[22] Filed: Jan. 23, 1995

[51] Int. Cl.$^6$ ................................................ A61M 29/00
[52] U.S. Cl. .................................. 604/96; 604/20; 604/21
[58] Field of Search ................................ 604/53, 96, 101, 604/892.1; 606/194

[56] References Cited

U.S. PATENT DOCUMENTS

| | | |
|---|---|---|
| 4,364,392 | 12/1982 | Strother et al. . |
| 4,417,576 | 11/1983 | Baran . |
| 4,994,033 | 2/1991 | Shockey et al. . |
| 5,047,028 | 9/1991 | Qian . |
| 5,087,244 | 2/1992 | Wolinsky et al. . |
| 5,098,381 | 3/1992 | Schneider . |
| 5,213,576 | 5/1993 | Abiuso et al. ............................. 604/96 |
| 5,232,444 | 8/1993 | Just et al. . |
| 5,236,413 | 8/1993 | Feiring ..................................... 604/96 |
| 5,282,785 | 2/1994 | Shapland et al. ......................... 604/96 |
| 5,286,254 | 2/1994 | Shapland et al. . |
| 5,318,531 | 7/1994 | Leone ....................................... 604/96 |

FOREIGN PATENT DOCUMENTS

| | | |
|---|---|---|
| 0372088A1 | 6/1990 | European Pat. Off. . |
| 1069826A | 1/1984 | U.S.S.R. . |
| 1146057A | 3/1985 | U.S.S.R. . |

OTHER PUBLICATIONS

Wolinsky et al., "Use of a Perforated Balloon Catheter to Deliver Concentrated Heparin Into the Wall of the Normal Canine Artery" *JACC*, vol. 15, No. 2, at 475–481 (1990).

*Primary Examiner*—Corrine M. McDermott
*Assistant Examiner*—N. Kent Gring
*Attorney, Agent, or Firm*—Merchant, Gould, Smith, Edell, Welter & Schmidt PA

[57] ABSTRACT

An apparatus for delivering an agent to a treatment area. The apparatus includes a catheter that has a distal portion and a proximal portion. The catheter defines a lumen. A pressure regulator is in fluid communication with the lumen. A selectively inflatable member is also in fluid communication with the lumen, and is formed from a membrane. The membrane has first and second portions. The first portion defines pores sized from about 0.05μ to about 1μ and has a pore density from about $10^6$ pores/cm$^2$ to about $10^9$ pores/cm$^2$. The flux rate is from about 0.001 ml/(min·cm$^2$·atm) to about 0.4 ml/(min·cm$^2$·atm). The second portion is substantially impermeable.

25 Claims, 3 Drawing Sheets

MICROPOROUS CATHETER

TECHNICAL FIELD

The present invention relates generally to a drug delivery apparatus and, more particularly, to a catheter with a microporous balloon for selectively and locally delivering a drug.

BACKGROUND

Many techniques currently exist for delivering drugs or other medicaments to body tissue. Examples of current techniques include oral administration; injection directly into body tissue, such as through an intramuscular injection; topical or transcutaneous administration where the drug is passively absorbed, or caused to pass, into or across the skin or other surface tissue; and intravenous administration, which involves introducing a selected drug directly into the blood stream.

Except for topical or transcutaneous administration, the above drug delivery systems tend to be systemic. In other words, administration of the drug is delivered throughout the body by the blood stream.

Systemic administration of a drug is effective for some treatments. However, this type of delivery involves tradeoffs because many therapeutic drugs are highly toxic and may cause dangerous side effects when the blood stream carries them to healthy tissue as well as diseased tissue. Thus, a physician must carefully balance the therapeutic benefit of a drug against the toxic side effects that the drug may cause. Additionally, many drugs are expensive and systemic delivery is not an economically efficient method to deliver drugs if the treatment area is limited to a confined region.

Transcutaneous drug delivery systems tend to be localized delivery systems in that the drug is delivered locally to a selected area. However, such drug delivery systems are limited to the application of a drug through the patient's skin or other surface tissue. Thus, the above described drug delivery systems are generally not appropriate for the localized treatment of internal body tissue.

Local drug delivery to a selected internal treatment area would facilitate and/or improve many treatments if the delivery is controlled and the drug is prevented from appreciably affecting tissue outside the treatment area. Such local delivery would allow the delivery of high dosages and concentrations of toxic drugs while reducing the risk of serious side effects. Local internal delivery is also economically efficient because the blood stream does not needlessly transport the drug to healthy tissue.

Percutaneous transluminal coronary angioplasty (PTCA), which dilates a narrowed vessel, is one type of application in which the local delivery of an agent would be advantageous. During PTCA, a catheter is inserted into the cardiovascular system under local anesthesia. An expandable balloon portion is then inflated to compress the atherosclerosis and dilate the lumen of the artery.

Despite the general success of PTCA procedures, the incidence rate of restenosis is 25% and may be as high as 50%. Additionally, as many as 45% of PCTA patients are at risk of acute thrombotic closure. However, the delivery of an appropriate drug during PTCA can limit or prevent restenosis and acute thrombotic closure. The difficulty is that many drugs that are used to prevent these conditions can cause very serious side effects. For example, hirudin and hirulog can cause significant bleeding. Additionally, hirudin can cause impaired renal function (i.e., shut down the patient's kidneys).

Medical researchers have tried various techniques to treat stenosed vessels including the use of lasers, application of heat and the use of intravascular stents. However, many of these are still under investigation with mixed results, while others have generally not been successful. Thus, the ability to administer a drug locally to the dilated portion of the artery in PTCA procedures, without significantly affecting other tissues, would greatly enhance the ability to address the restenosis problem.

The treatment of cancerous tumors or the like is a second example of a medical application in which local drug delivery is beneficial. In the treatment of such tumors, an objective is to administer the cancer drug so that it is localized in the tumor itself. Such drugs are commonly administered systemically through the bloodstream. Various means are then utilized for causing the drug to localize in the cancer tumor. Nevertheless, significant portions of the drugs still circulate through the bloodstream, thereby affecting non-cancerous tissue, producing undesirable side effects, and limiting the dosage of the drug that can be safely administered.

One type of apparatus that has been tried for local drug delivery is a catheter that has a perforated balloon. Early designs typically contemplated the use of a macroporous balloon (i.e., a balloon that has large perforations). This type of design has several shortcomings. For example, a macroporous balloon may realize leakage of inflation fluid during inflation; blood ingress into the balloon during deflation; and have an inability to develop sufficient vacuum in the balloon to either deflate quickly, or to fully deflate thereby providing a low profile for removal; and an inability to decouple balloon inflation from drug delivery.

Minimizing the number of perforations is one solution that has been tried to overcome these shortcomings. However, reducing the number of perforations does not fully address these problems (e.g. blood ingress) and may cause additional shortcomings. For instance, having only a few perforations may result in non-uniform distribution of the drug. Blockages of a few perforations will significantly reduce the amount of drug that can be administered and also makes drug distribution even less uniform.

Additionally, a minimal number of perforations provides only a few paths for the electric current during iontophoresis. The current that flows through the perforations may have a high density and damage the adjacent tissue.

Another problem that results from having a limited number of pores is jetting. The high pressure used during inflation will force the fluid through the perforations at a high velocity, which damages the adjacent tissue. Examples of the damage that can result from jetting include direct tissue damage, formation of edema, and rupturing of the vessel. Additionally, vascular damage due to jetting can lead to the development of intimal hyperplasia, which ultimately results in restenosis.

Accordingly, there is a need in the art for an apparatus that is capable of locally delivering an agent without causing serious tissue damage and that can quickly and completely deflate, thereby increasing maneuverability. There is also a need for such an apparatus that minimizes systemic delivery of the agent and thus reduces side effects. Such an apparatus would be useful for the localized treatment of internal body tissue to limit restenosis following PTCA, to treat cancerous tumors or the like, or to treat other types of maladies.

SUMMARY

In accordance with the present invention, an apparatus for delivering a drug to a treatment area includes a catheter that has a distal portion and a proximal portion. The catheter defines a lumen. A selectively inflatable member having a single chamber is in fluid communication with the lumen, and is formed from a membrane that has pores sized from about 10 Å to about 1μ. The pore density is from about $10^4$ pores/cm$^2$ to about $10^{11}$ pores/cm$^2$.

DETAILED DESCRIPTION

Figure 1:
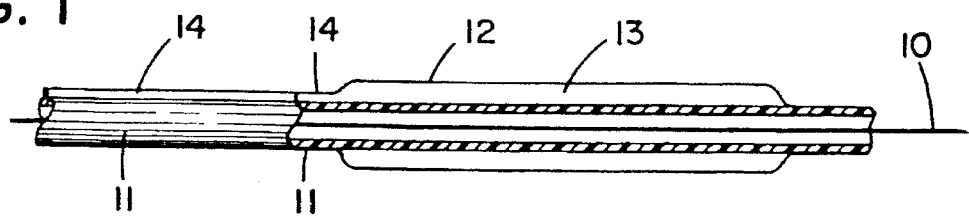
FIG. 1 is a fragmentary view, partially in section, of a first embodiment of the drug delivery apparatus of the present invention in the form of a catheter with a modified dilatation balloon in its deflated state.

A preferred embodiment of the present invention will be described in detail with reference to the drawings, wherein like reference numerals represent like parts and assemblies throughout the several views. Reference to the preferred embodiment does not limit the scope of the invention, which is limited only by the scope of the claims attached hereto.

FIGS. 1–6 illustrate the preferred and various alternate designs of the delivery apparatus used in accordance with the present invention. In general, the present invention relates to a microporous balloon that can be used in conjunction with existing catheters. Such an apparatus can deliver an agent or combination of agents to or through a localized treatment area of a passageway with minimal undesirable effect on other body tissue. The treatment area can be a localized area of the passageway or a localized area of tissue located adjacent to the passageway. A catheter that embodies the present invention can also be used with an introducer such as a probe or a trocar to treat internal body tissue such as a tumor.

An agent can be any type of substance that is used for medical purposes such as a drug, fixative, diagnostic dye, biological agent, antisense, or gene. The term catheter as used in the present application is intended to broadly include any medical device designed for insertion into a body passageway for medical purposes including the injection or withdrawal of fluids and maintaining a passage opening.

FIG. 1 illustrates the distal end of a catheter that includes a microporous balloon 12 in a deflated state. The catheter includes a guide wire 10, an elongated, flexible catheter body 11, a selectively inflatable member or microporous balloon 12 positioned on the catheter body 11 near its distal end, and a balloon lumen or passageway 14 extending along the catheter body 11 to the proximal end of the body 11. The lumen 14 is in fluid communication with the microporous balloon 12, which defines a single chamber 13.

Figure 2:
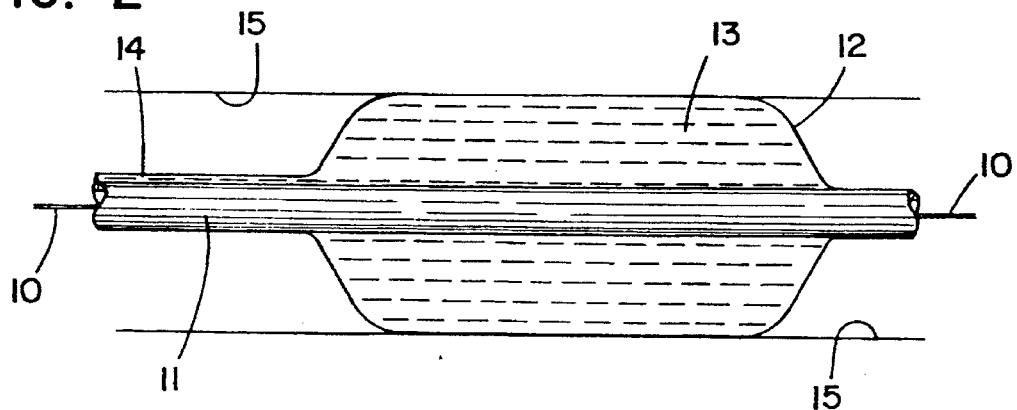
FIG. 2 is a fragmentary view, partially in section, of the drug delivery apparatus of FIG. 1 positioned in a blood vessel with the dilatation balloon in its inflated state.

FIG. 2 illustrates the microporous balloon 12 in an inflated state and positioned within a passageway 15. In use, the microporous balloon should be positioned adjacent to the treatment area. The balloon 12 is inflated by introducing the agent through the lumen 14 and into the chamber 13 of the microporous balloon 12. The pressure of the agent within the balloon 12 causes the balloon 12 to expand until it comes into contact with the walls of the passageway. The agent can then be delivered from the microporous balloon 12 to the treatment area. The passageway can be a blood vessel, urethra, or any other bodily passage.

The microporous balloon 12 can be formed from either a permeable or a semi-permeable membrane, although a semi-permeable membrane is preferred. Additionally, the membrane that forms the microporous balloon 12 has either ultrafiltration or microfiltration membrane characteristics and is made from a material that is suitable for forming a balloon. Examples of suitable membrane materials are polyester, polyolefin, fluorpolymer, and polyamide.

The pores defined by the membrane can range in size from about 10 Å to 1μ. The pore density can range from about $10^4$ to $10^{11}$ pores per cm$^2$, and the thickness of the membrane can range from about 5μ to 15μ. These characteristics can be varied in order to control the flux rate of the agent that passes through the membrane during delivery. The flux rate is determined in units of ml/(min·cm$^2$·atm) and can range from about 0.001 units to 0.4 units. The preferred range is from about 0.005 units to 0.1 units.

The flux rate, pore size, pore density, and membrane thickness are roughly interrelated in the following manner. The flux rate is directly proportional to the pore density, all other characteristics being constant. Similarly, the flux rate is proportional to the diameter of the pore raised by a power of four. The flux rate is inversely proportional to the thickness of the membrane.

Two related examples demonstrate several advantages of the present invention. The first example relates to the flow rate of a microporous balloon. The second example relates to jetting effects.

The first example compares a porous balloon containing 100 perforations having a 25μ diameter and a microporous membrane containing $10^8$ pores having a 0.1μ diameter. The example demonstrates the advantage of the present invention over a typical porous balloon. As stated above, the flow rate of liquid through a pore is approximately proportional to the diameter of the pore raised to the fourth power. At a given pressure, therefore, the relative flow rates of a traditional porous balloon and a microporous balloon during inflation is:

$$\frac{\text{flow of macroporous}}{\text{flow of microporous}} = \frac{(100)(25)^4}{(10^8)(0.1)^4} = 39$$

The flow rate of the macroporous balloon is 39 times greater than the flow rate of the microporous balloon.

This example demonstrates that the traditional porous balloon has a much higher flow rate of liquid when under pressure. The practical result of the higher flow rate is that the porous balloon will leak more fluid during inflation than the microporous balloon. Leaking fluid during inflation is a significant shortcoming because the agent may get carried off in the patient's blood stream and adversely effect healthy tissue.

An advantage of the microporous balloon of the present invention is that leaking is minimized. In turn, the effect of the agent on healthy tissue is also minimized. This advantage can be significant when delivering toxic agents.

A related advantage is that balloon inflation and delivery of the agent can be effectively decoupled with the microporous balloon because the balloon will lose very little agent during inflation. The agent can be delivered after the balloon has been inflated. If pressure is used to deliver the agent, the pressure in the balloon can be merely increased to deliver the agent. If some type of phoresis is used to deliver the agent, the phoresis mechanism can be employed. This approach applies to essentially any driving mechanism. In contrast, the agent will leak out of a traditional porous balloon during the initial inflation and hence be delivered to the patient systemically.

In order to overcome the leakiness of traditional porous balloons during inflation, many designs include extra components such as an inner balloon or an expandable cage, which are used for inflation. The difficulty with these added components is that they increase the diameter of the deflated balloon. The present invention does not need these additional components and hence the diameter or profile of the deflated microporous balloon 12 is minimized.

Furthermore, the lower flux rate of a microporous balloon makes it easier to develop a negative pressure in the balloon during deflation. Thus, the microporous balloon 12 can be deflated to a low profile upon completion of the delivery. Having a small diameter of the deflated balloon permits the catheter to be more easily inserted into, withdrawn from, and maneuvered within the patient's body.

The second example compares the velocity of the fluid as it passes through 25μ pores of a macroporous balloon and 0.1μ pores of a microporous balloon. The average velocity at which fluid moves through a given pore is approximately proportional to the square of the pore diameter. Thus, the relative velocities of these two balloons are related as follows:

$$\frac{\text{velocity of macroporous}}{\text{velocity of microporous}} = \frac{(25\mu)^2}{(0.1\mu)^2} = 62,500$$

The velocity of the macroporous balloon is 62,500 times greater than the velocity of the microporous balloon.

This high velocity phenomena of a macroporous balloon is called a jetting effect and can cause significant tissue damage during delivery of an agent. This second example demonstrates that the microporous balloon of the present invention has an advantage because the agent is delivered at a much lower velocity and the risk of tissue damage is significantly reduced.

Additionally this jetting effect can be controlled independently of the flow rate. In other words, the flow rate of delivery can be increased without increasing the velocity of the fluid as it passes through the pores. The volumetric flow rate of a fluid can be increased by increasing the pore density, which will provide the desired effect and delivery rate without increasing the fluid velocity.

Some earlier designs have tried to overcome this jetting effect by providing a balloon that has two concentric walls that define a second balloon chamber. The problem with this design is that the diameter of the balloon is increased and thus more difficult to maneuver in small passageways. The balloon is also more difficult to compress by creating a vacuum force. Additionally, a balloon with concentric walls is more difficult to manufacture.

The present invention has other advantages in addition to those demonstrated by the previous examples. One additional advantage is that the 25μ perforations in the porous balloon will allow influx of red blood cells (≈8μ diameter), platelets (≈2μ), neutrophils (≈16μ), and other blood components and secretions during deflation. The influx of blood components or other secretions will tend to plug the perforations and contaminate the interior of the balloon. In fact, it is likely that the effective porosity of the balloon will be compromised after only a single deflation.

In sharp contrast, the microporous membrane will allow minimal influx of blood components or secretions. As a result, multiple inflations of a microporous balloon are much more likely to be successful. The advantages of performing multiple inflations are apparent when treating multiple lesions within a given patient. Advantages are also apparent when a significant length of time is required to deliver a single dose of the agent and hence multiple inflations or a perfusion catheter are required.

Another advantage relates to the high pore density in the microporous balloon 12. Because of the great number of pores, the areal density of a microporous balloon is greater than the areal density of a traditional porous balloon. The areal density is the pore density times the cross-sectional area of a single pore.

In the examples above, the areal density is 0.8% for the microporous balloon and only 0.05% for the porous balloon. Thus, the microporous balloon provides more surface area for delivery of the agent than the porous balloon, and the agent is distributed more uniformly across the interior surface of the vessel. Uniform distribution along the vessel enables uniform penetration of the agent into the internal tissue that forms the treatment area.

The increased areal density also eliminates the risk of hot spots created by the electric current because the current density is lower, and the electric current is more evenly distributed throughout the treatment area. Additionally, the increased density means that the microporous balloon of the present invention will have many more pores than a macroporous balloon. Thus, any plugging of pores in a microporous balloon will have less overall impact than in a porous balloon. A further advantage of the present invention is that leakage through side branches is reduced.

It is contemplated that the particular material from which the balloon 12 is constructed will depend to some extent on the specific composition of the agent to be delivered as well as the pressures that are developed within the balloon chamber 13. In the structure of FIGS. 1 and 2, the microporous balloon 12 can be constructed from either elastomeric or nonelastomeric materials. The pressure within the chamber 13 that is required to transport the agent across the microporous membrane that makes up the balloon walls typically is between about 1 atm and 12 atm. However, the preferred range is between about 3 and 10 atm.

Figure 3:
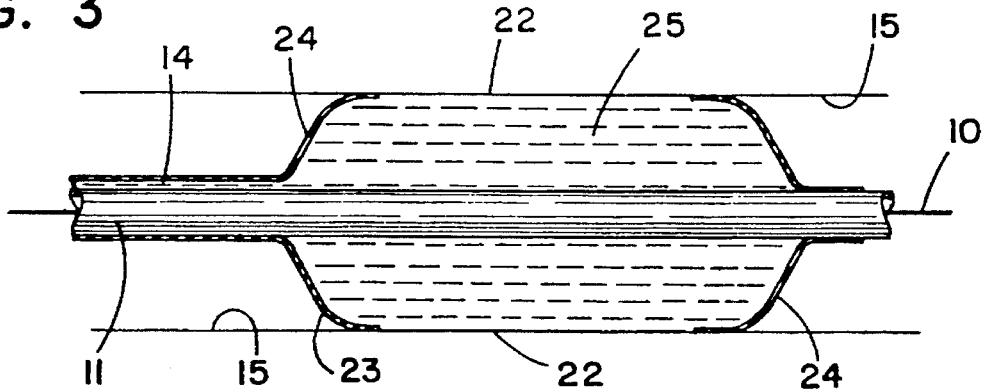
FIG. 3 is a fragmentary view, partially in section, of a further embodiment of the drug delivery apparatus of the present invention positioned in a blood vessel.
Figure 4:
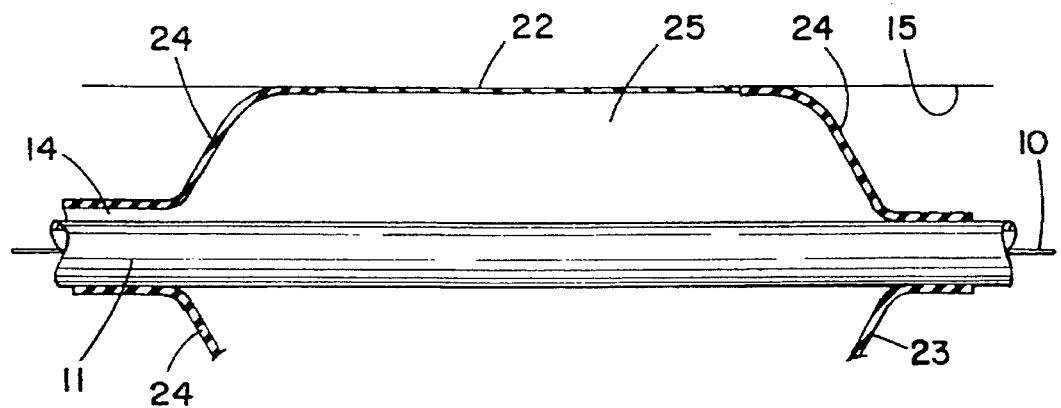
FIG. 4 is an enlarged fragmentary view, partially in section, of the embodiment of FIG. 3.

Referring to FIGS. 3 and 4, an alternative embodiment of the present invention has a balloon 23 that has a microporous portion 22 and impermeable portions 24 at oppositely disposed ends of the balloon. The microporous portion 22 is positioned between the impermeable portions 24. This alternative embodiment enables more specific and precise delivery of the agent because the agent that is contained in the chamber 25 can pass only through microporous portion 22. Passage of the agent through the end portions 24 is prevented.

In one possible design of the catheter shown in FIGS. 3 and 4, the microporous portion 22 and the impermeable portions 24 are made from two different materials. The material that forms the impermeable portions 24 may be made from a material such as polyethylene or polyester. The material that is used to form the microporous portion is the same as the material that forms the microporous balloon 12 that is shown in FIGS. 1 and 2.

In another possible design, the balloon 23 is made from a single type of material. If a single type of material is used, the impermeable portions can be formed in several different ways. For example, the impermeable portions 24 can be significantly thicker than the microporous portion 22. The extra thickness of the impermeable portions 24 makes them substantially impermeable. Alternatively, the impermeable portions 24 can be formed by masking the end portions of the balloon 12 during a track-etch process. Track-etch manufacturing technology is discussed in more detail below. One skilled in the art will realize that other design and manufacturing techniques can be used to create a balloon that has both a microporous portion and an impermeable portion.

In the embodiments of FIGS. 1–4, pressure is the force that is utilized to transport the agent from the balloon chamber to the vessel wall. A conventional pressure regulator can be used to apply sufficient pressure to deliver the agent across the membrane and to the targeted area. Examples of a pressure regulator include a compressor, syringe, or syringe pump. One skilled in the art will recognize that the pressure should be adequate to drive the agent across the microporous membrane to the treatment area without further traumatization of internal body tissue.

Additionally, a fluid enhancement composition can be used to increase penetration of the agent through a vessel wall. One type of fluid enhancement composition includes the carrier DMSO. Other examples include propylene glycol, azone, and ionic or non-ionic surfactants.

The present invention can also utilize iontophoresis technology, which drives ionic agents or drags nonionic agents that are in an ionic solution. In order for iontophoresis techniques to be utilized, therefore, the agent to be delivered has an ionic nature or is bound to other ionic molecules. Iontophoresis is useful in certain applications of the present invention because it facilitates both transport of the agent across the wall of the microporous balloon and enhances tissue penetration.

Figure 5:
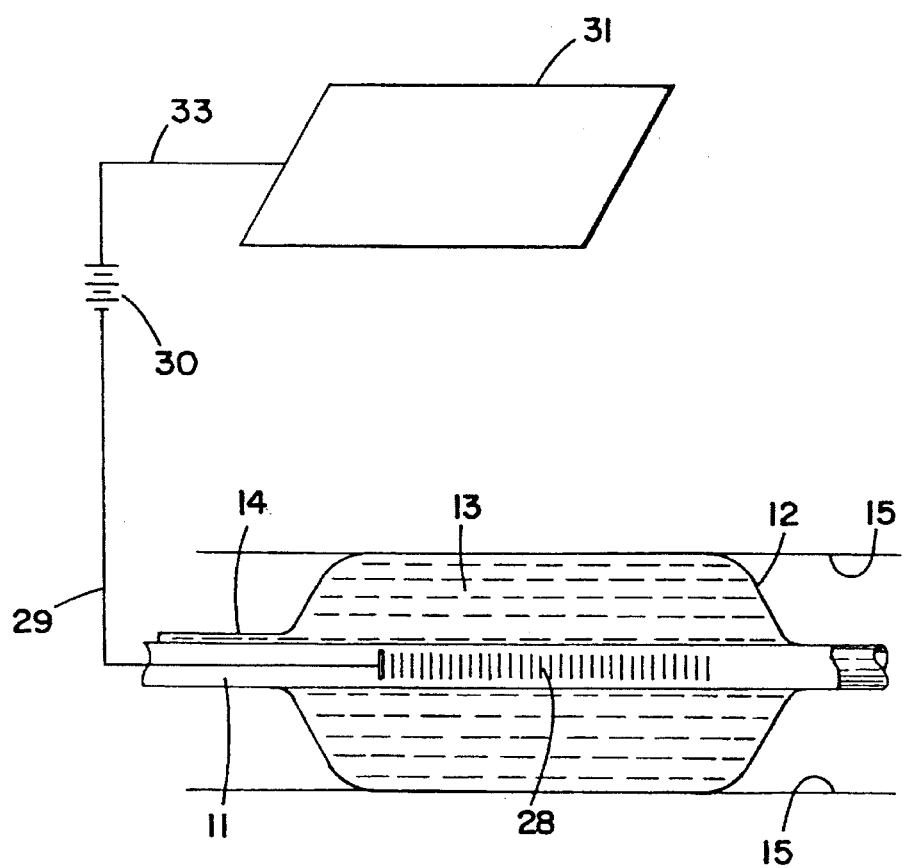
FIG. 5 is a fragmentary view, partially in section, of the drug delivery apparatus of the present invention positioned in a blood vessel and embodying iontophoresis means to transport the drug across the balloon surface.

The embodiment of the present invention shown in FIG. 5 is substantially identical to the embodiment shown in FIGS. 1 and 2. The primary difference is that the embodiment shown in FIG. 5 utilizes iontophoresis to transport the agent from the chamber 13 to the wall of the passageway 15.

More specifically, a first electrode 28 is located on or within the catheter body 11 and connected to a power supply 30 by a lead 29. A second electrode 31 is located either on the surface or within the patient's body and is connected to the power supply 30 by a lead 33. The power supply 30 provides an electric current between the first and second electrodes 28 and 31. The current can be direct or have a particular wave form. Examples of possible wave forms include a rectangular wave having a frequency of about 100 Hz or greater. Additionally, a series of waves can be intermittently passed between the electrodes 28 and 31 during the process of delivering an agent.

An additional advantage of the present invention is realized when iontophoresis is used during delivery of the agent. The result is a uniform path for the electric current and a reduced potential for areas of high electric current densities. Reducing the area for high current densities reduces the potential for tissue damage or breakdown of the membrane material.

Figure 6:
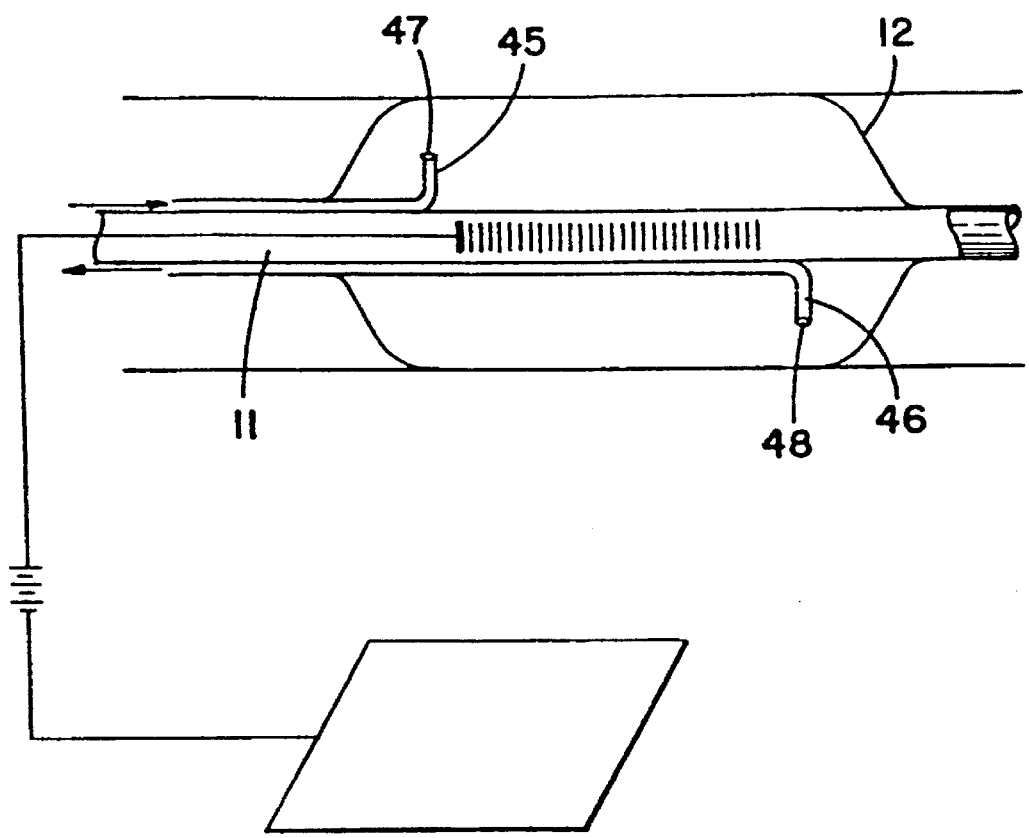
FIG. 6 is a fragmentary view, partially in section, of the drug delivery apparatus of the present invention positioned in a blood vessel, embodying iontophoresis to transport a drug across the balloon surface where the solution containing the drug is circulated through the balloon.

Referring to FIG. 6, an alternative embodiment of the present invention has a microporous balloon 12 that is positioned on catheter body 11 near its distal end. A delivery lumen or passageway 45 has a port 47 and extends along the catheter body 11 to the proximal end of the catheter body 11. A recovery lumen or passageway 46 has a port 48 and also extends along the catheter body 11 to the proximal end of the catheter body 11. The ports 47 and 48 are in fluid communication with the chamber 13 of microporous balloon 12.

The delivery lumen 45 and recovery lumen 46 are useful for circulating solution containing an agent to and from the catheter balloon. Circulation is useful in delivering agents that are difficult to dissolve. In such a situation, the delivery solution typically has a very low concentration of the agent and is easily depleted of such agent. Because the delivery solution has a low concentration of the agent, fresh delivery solution is injected into the chamber through the delivery lumen 45 and depleted solution is withdrawn through the recovery lumen 46. Circulation is also important for continuous delivery over long time periods. A recovery lumen is also useful for exchanging agents within the chamber 13 of the microporous balloon 12.

One skilled in the art will realize that during delivery of the agent, the amount of agent that is injected through the delivery lumen 45 and the amount of the agent that is withdrawn through recovery lumen 46 should be adjusted so that the microporous balloon 12 is maintained in an inflated state. The ports 47 and 48 are positioned in the chamber 13 in order to achieve optimal circulation of the agent within the microporous balloon 12.

Phonophoresis (sometimes referred to as sonophoresis) is an alternative transport force that uses ultrasonic or high frequency sound waves to transport an agent. As used in the present invention, phonophoresis can transport agents through the microporous membrane and into the surrounding tissue. Phonophoresis has several advantages over iontophoresis for certain therapeutic procedures, including the ability to achieve greater penetration into the internal body tissue. Phonophoresis also has the ability to more readily deliver an entire molecule and is not limited to delivering only ionically charged forms of the agent.

In addition to delivering an agent, ultrasound is advantageous because it increases tissue temperature, tissue hyperemia, and capillary permeability. These additional results enhance intra-tissue transport of an agent, enhance cellular uptake, and cause vasodilation/relaxation, which may be beneficial in vascular applications of the present invention.

Referring to FIGS. 5 and 6, a catheter that uses phonophoresis replaces the first electrode 28 with an ultrasonic piezoelectric transducer (barium titanate, lead zirconate titanate, or the like) that is connected to power supply 30. The second electrode 31 is not needed in this embodiment. In use, the ultrasonic transducer is activated to enhance transport of agents into tissue surrounding the catheter. The diffusion rate of agents delivered by phonophoresis depends upon the intensity and frequency of the ultrasonic field.

Prior transdermal applications of phonophoresis use intensities between 0.1 and 6 watts/cm. In these applications, there is a direct correlation between the amount of the agent that is diffused and the intensity of the ultrasonic field. Internal applications (not requiring transdermal delivery) of phonophoresis with the embodiments of the present invention are envisioned to require significantly less intensity to deliver an equal amount of drug.

Additionally, phonophoretic delivery apparatuses can use various frequencies of sonic waves. Earlier devices that were used for transdermal phonophoresis typically emitted sonic waves having a frequency of about 1 MHz. It is envisioned that the present invention can use a frequency of about 1 MHz or less for internal applications of phonophoresis.

Although the driving forces are described independently, one skilled in the art will realize that any combination of the driving forces can be used simultaneously to enhance delivery of an agent. For example, a fluid enhancement composition can be used with pressure, iontophoresis, or phonophoresis. Similarly, pressure can be used in combination with iontophoresis or phonophoresis.

The microporous membrane of the present invention can be manufactured using track-etch technology. In this process, a nonporous balloon is exposed to ion bombardment that induces damage tracks normal to the balloon surface. Examples of ions include protons, electrons, atomic nuclei, and various forms of radiation. Then, the damage tracks are controllably etched to provide a porous membrane that has pores of a known, uniform diameter. The number of pores is equal to the number of damage tracks and can be controlled by the dose of the ion bombardment. This process provides very good control of the process while allowing flexibility to produce pore sizes from less than $0.10\mu$ up to tens of microns and pore densities from 1 pore/cm$^2$ to $10^{11}$ pores/cm$^2$ or higher.

During the manufacturing process, the unique geometry of the microporous balloon in the present invention can be accommodated by techniques that are used to process hollow fibers and other 3-dimensional substrates. These techniques involve flattening the nonporous balloon so that most areas of the balloon are substantially perpendicular to the particle beam during ion bombardment. Those areas of the balloon that are to remain nonporous do not need to be flattened.

In order to illustrate the present invention and its use in the treatment of a localized area of a passageway, the specific application of the present invention to the reduction of restenosis will be described. Following a discussion of reducing restenosis, the present invention will be applied to the treatment of tumors. Although only these two types of applications are described in detail, one skilled in the art will realize that the present invention can be used in a variety of other applications.

Percutaneous transluminal coronary angioplasty (PTCA) is a proven procedure for the treatment of atherosclerosis and other conditions that tend to narrow arterial passageways. Despite the generally excellent success of PTCA, relatively high restenosis (the tendency of the dilated artery to close) rates continue to be a major problem. Restenosis can include gradual reclosure as well as abrupt reclosure that results from conditions such as thrombotic occlusion and vasospasms.

In order to prevent restenosis, an agent referred to as a fixation solution or a fixative is delivered locally to the dilated portion of the vessel. The fixative renders the vessel wall biologically inert in order to prevent or reduce reactions that lead to reclosure. Because many fixatives are toxic and/or generally harmful if they contact healthy tissue, they can cause serious side effects if significant doses are delivered systemically. Therefore, it is essential that only the dilated portion of arterial wall is exposed to the fixative.

Thus, a catheter having a microporous balloon during PTCA procedures is advantageous because it has a minimal amount of leakage, and exposure to the agent is substantially limited to the treatment area. Minimizing leakage is especially important given the type of damage an agent can cause to healthy tissue outside the desired treatment area.

In accordance with the preferred apparatus of the present invention, the agent may consist of compounds or drugs to reduce vasomotor action (calcium antagonists) and inflammatory response (steroids) as well as anticoagulants. Calcium antagonists may include materials such as diltiazem HCl, nifedipine and verapamil HCl, steroids such as dexamethasone and specific nonsteroidal anti-inflammatory agents. Anticoagulants may include materials such as heparin, hirudin, dipyridamole, papaverine HCl, ethaverine HCl and prostacyclin inhibitors. It is also contemplated that agents (antisense, growth inhibitor, or gene therapy) inhibiting smooth muscle proliferation, which is a primary factor in restenosis, or agents tending to reduce collagen response to injury could also be used. Fibroblast proliferation inhibiting agents may also be included as well as collagen response reduction agents. It is still further contemplated that compounds that reduce platelet aggregation may also be beneficial to administer. Also, antitumor or other antimitogenic agents can be used for prevention of restenosis.

The embodiment shown in FIGS. 1 and 2 are used for PTCA procedures in the following manner. The guide wire 10 is first inserted into the selected artery to a point past the stenotic lesion. The catheter including the catheter body 11 and microporous balloon 12 is then advanced along the guide wire 10 to the desired position in the arterial system so that the microporous balloon 12 traverses or crosses the stenotic lesion. The microporous balloon 12 is then inflated by introducing an inflation fluid through the balloon lumen 14 into the chamber 13. During inflation, the outer surfaces of the microporous balloon 12 press outwardly against the inner surfaces of the vessel wall 15. Expansion or dilation of the vessel in the area of the stenotic lesion is accomplished by the application of high pressure, which results in simultaneous dilation and drug delivery without excessive drug loss or vascular damage due to jetting. The pressure inside the balloon is not great enough to cause more than a minimal amount of agent to escape from the balloon 12 until the microporous balloon is in contact with the wall of the vessel.

Alternatively, the catheter of FIGS. 1 and 2 may be used after dilation was previously achieved by another catheter. In this case, the microporous balloon 12 is expandable in order to bring it into contact with the vessel wall for delivery of an agent. Again, the pressure inside the balloon is not great enough to cause delivery of the agent until the microporous balloon is in contact with the wall of the vessel.

After delivery of the agent is complete, the microporous balloon 12 is deflated and either removed from the patient's body or maneuvered to a different location for treatment of another stenotic lesion. The embodiments shown in FIGS. 3 and 4 are used in substantially the same procedure. This procedure is not described in detail for purposes of clarity and brevity.

During operation of the embodiment shown in FIG. 5, the balloon 12 is positioned in the passageway 15. The balloon interior 13 is then inflated with the agent through the lumen 14. As the balloon expands, it causes the artery to dilate. The second electrode 31 is then placed against the patient's skin or within the patient's body. This is followed by activating the power supply 30, thereby creating a current between the first and second electrodes 28 and 31 that passes through the balloon wall 26.

The current drives or drags the agent from the chamber 13, through the pores in the microporous balloon 12, and into the treatment area. The structure of FIG. 5 utilizes both pressure and iontophoresis as the driving force. Iontophoresis, however, could be utilized alone. The polarity of the iontophoretic electrodes may be reversed in order to recapture excess agent delivered to or through the vessel wall.

The embodiment that utilizes phonophoresis can also be used in combination with pressure to drive the agent from the chamber 13 to the treatment area. This embodiment is used in a similar manner to the iontophoresis embodiment shown in FIG. 5 except that the second electrode is not required and ultrasonic waves are emitted from the transducer rather than an electrode.

The embodiment shown in FIG. 6 can also be used for PCTA. The operation of this embodiment is substantially similar to the other embodiment except that agent is circulated through delivery and recovery lumens 45 and 46. Circulation of the agent was discussed above.

In addition to delivering an agent to a vessel wall, the embodiments shown in FIGS. 1–6 are also useful for delivering an agent to or through a vessel wall. For example, the present invention can be used to deliver an antitumor, antihyperplastic, or other agent through a vessel wall to internal body tissue such as a nearby or adjacent tumor. In such an application, an agent is delivered substantially transversely to the longitudinal axis of a body passageway in order to treat a localized region of tissue located adjacent to the passageway. This can be accomplished by using iontophoresis to drive, or DMSO to carry, the agent through the passageway wall and into the surrounding or adjacent tissue. Any of the foregoing alternative embodiments of the apparatus as seen in FIGS. 1–6 may also be used for such delivery.

In particular, tumors may be treated by delivering certain agents through blood vessels or the intestinal tract, or other passageway or cavity to adjacent tumor sites. Examples of such agents include mechlorethamine, cyclophosphamide, chlorambucil (leukeran), melphalan (alkeran), busulfan (myleran), dacarbazine (DTIC), cisplatin (Platinol), methotrexate, 6-mercaptopurine 6-MP, thioguanin 6-TG, 5-fluorouacil (5-FU), vinblastine (velban), dactinomycin, doxorubicin, daunorubicin, mitomycin (mutamycin), diethylstilbestrol, and retinoic acid and analogues. The present invention also is well suited to delivery of sensitizer and immunomodulator drugs.

One skilled in the art will realize that the embodiments of the present invention can be modified for insertion into and delivery to a treatment area that consists of internal body tissue such as a tumor. Initially, the position of the treatment area is determined mechanically, radiographically, thermally, ultrasonically, or through a similar methodology. An introducer (not shown) is then placed into the treatment area after identification of its position.

The introducer can be designed for steerability to facilitate positioning into the tumor. One way to accomplish steerability is to simply place a bend in the introducer. Other mechanical design techniques known to those skilled in the art also can be utilized. The inducer can be any type of trocar or probe that is conventional in the art.

The catheter is then passed over the inducer or through the void left in the intervening tissue by the withdrawal of the introducer. After the catheter is in place, as confirmed by one of the foregoing methods, the active compound is delivered from a chamber, through the pores of a microporous membrane, and into the local or regional tissue. The active compounds delivered to an internal body tissue using the present invention, but are not limited to, antitumor agents such as the vinca alkaloids, anthracycline antibiotics, platinum analogs, antimetabolites (e.g., methotrexate); antibiotics; sensitizers or other compounds such as those exemplified above.

The advantage of this method is that it allows delivery of the agent into the interstitial fluid and into the cells of the target area themselves even if the vasculature of the area is severely compromised and the cells do not preferentially take up the agent. These phenomena are a well-known attribute of solid tumors and constitute one of the most significant barriers to the treatment of such cancers.

In addition to delivery of antitumor agents to internal tissues, the usefulness of the present apparatus and method for the treatment of other diseases of internal tissue will be appreciated by those skilled in the art.

While the invention has been described in conjunction with a specific embodiment thereof, it is evident that different alternatives, modifications, and variations will be apparent to those skilled in the art in view of the foregoing description. Accordingly, the invention is not limited to these embodiments or the use of elements having specific configurations and shapes as presented herein.

The invention that we claim is:

1. An apparatus for delivering an agent to a treatment area using pressure, the apparatus not including phoretic delivery means, the apparatus comprising:

a catheter having a distal portion and a proximal portion, the catheter defining a lumen;

a selectively inflatable member in fluid communication with the lumen, wherein the selectively inflatable member is formed from a membrane having pores sized from about 10 Å to about 1µ and a pore density from about $10^4$ pores/cm$^2$ to about $10^{11}$ pores/cm$^2$, further wherein the selectively inflatable member has a single chamber.

2. The apparatus of claim 1 wherein the membrane is arranged and configured to deliver the agent at a flux rate from about 0.001 ml/(min·cm$^2$·atm) to about 0.4 ml/(min·cm$^2$·atm).

3. The apparatus of claim 2 wherein the membrane is arranged and configured to deliver the agent at a flux rate from about 0.005 ml/(min·cm$^2$·atm) to about 0.1 ml/(min·cm$^2$·atm).

4. The apparatus of claim 1 wherein the pores are sized from about 0.05µ to about 1µ.

5. The apparatus of claim 4 wherein the pores are sized from about 0.08µ to about 0.5µ.

6. The apparatus of claim 1 wherein the pore density is from about $10^6$ pores/cm$^2$ to about $10^9$ pores/cm$^2$.

7. The apparatus of claim 6 wherein the pores have a nominal size of about 0.05µ and a pore density from about $10^8$ pores/cm$^2$ to about $10^9$ pores/cm$^2$.

8. The apparatus of claim 6 wherein the pores have a nominal size of about 0.1µ and a pore density from about $10^7$ pores/cm$^2$ to about $10^8$ pores/cm$^2$.

9. The apparatus of claim 6 wherein the pores have a nominal size of about 0.2µ and a pore density from about $10^6$ pores/cm$^2$ to about $10^7$ pores/cm$^2$.

10. The apparatus of claim 1 wherein the membrane that forms the selectively inflatable member is a continuous membrane.

11. The apparatus of claim 10 wherein the continuous membrane has a substantially uniform thickness.

12. The apparatus of claim 10 wherein the continuous membrane is seamless.

13. The apparatus of claim 12 wherein the continuous membrane has a portion that is substantially cylindrical and has oppositely disposed end portions, further wherein the oppositely disposed end portions tapper toward the catheter.

14. The apparatus of claim 13 wherein at least one of the oppositely disposed end portions is substantially impermeable.

15. The apparatus of claim 14 wherein both oppositely disposed end portions are substantially impermeable thereby causing the agent to be delivered in a substantially radial direction.

16. An apparatus for delivering an agent to a treatment area, the apparatus comprising:

a catheter having a distal portion and a proximal portion, the catheter defining a lumen;

a selectively inflatable member in fluid communication with the lumen, wherein the selectively inflatable member is formed from a seamless and continuous membrane having pores sized from about 10 Å to about 1μ and has a pore density from about $10^4$ pores/cm$^2$ to about $10^{11}$ pores/cm$^2$, further wherein the selectively inflatable member has a single chamber and oppositely disposed end portions, still further wherein at least one of the oppositely disposed end portions is substantially impermeable.

17. An apparatus for delivering an agent to a treatment area, the apparatus comprising:

a catheter having a distal portion and a proximal portion, the catheter defining a lumen;

a selectively inflatable member in fluid communication with the lumen, wherein the selectively inflatable member is formed from a seamless and continuous membrane, has pores sized from about 10 Å to about 1μ, has a pore density from about $10^4$ pores/cm$^2$ to about $10^{11}$ pores/cm$^2$, and is arranged and configured to deliver the agent at a flux rate from about 0.001 ml/(min·cm$^2$·atm) to about 0.4 ml/(min·cm$^2$·atm), further wherein the selectively inflatable member has a single chamber and oppositely disposed end portions, still further wherein at least one of the oppositely disposed end portions is substantially impermeable.

18. An apparatus for delivering an agent to a treatment area, the apparatus comprising:

a catheter having a distal portion and a proximal portion, the catheter defining a lumen;

a selectively inflatable member in fluid communication with the lumen, wherein the selectively inflatable member is formed from a seamless membrane, the membrane having a portion that is substantially cylindrical, the substantially cylindrical portion having pores sized from about 10 Å to about 1μ, a pore density from about $10^4$ pores/cm$^2$ to about $10^{11}$ pores/cm$^2$, further wherein the membrane is arranged and configured to deliver the agent at a flux rate from about 0.001 ml/(min·cm$^2$·atm) to about 0.4 ml/(min·cm$^2$·atm), still further wherein the selectively inflatable member has a single chamber and oppositely disposed end portions, the oppositely disposed end portions being substantially impermeable.

19. An apparatus for delivering an agent to a treatment area, the apparatus comprising:

a catheter having a distal portion and a proximal portion, the catheter defining a lumen;

a selectively inflatable member in fluid communication with the lumen, wherein the selectively inflatable member is formed from a membrane having pores sized from about 10 Å to about 1μ and a pore density from about $10^4$ pores/cm$^2$ to about $10^{11}$ pores/cm$^2$, the membrane being arranged and configured to deliver the agent at a flux rate from about 0.001 ml/(min·cm$^2$·atm) to about 0.4 ml/(min·cm$^2$·atm), further wherein the selectively inflatable member has a single chamber; and means configured to phoretically transport the agent from the chamber to the treatment area, the means being operably connected to the catheter.

20. The apparatus of claim 19 wherein the means configured to phoretically transport the agent includes first and second electrodes configured to be connected to a power supply, the first electrode being positioned within the chamber.

21. The apparatus of claim 19 wherein the means configured to phoretically transport the agent includes an ultrasonic transducer positioned within the chamber.

22. The apparatus of claim 19 wherein the membrane is arranged and configured to deliver the agent at a flux rate from about 0.005 ml/(min·cm$^2$·atm) to about 0.1 ml/(min·cm$^2$·atm).

23. The apparatus of claim 19 wherein the membrane that forms the selectively inflatable member is a continuous membrane.

24. The apparatus of claim 23 wherein the continuous membrane has a substantially uniform thickness.

25. The apparatus of claim 23 wherein the continuous membrane is seamless.

* * * * *